United States Patent
Ramadhyani et al.

(10) Patent No.: US 10,390,871 B2
(45) Date of Patent: Aug. 27, 2019

(54) CRYONEEDLE

(71) Applicant: Galil Medical Inc., Arden Hills, MN (US)

(72) Inventors: Satish Ramadhyani, Minneapolis, MN (US); Andrew Kevin Zachman, St. Michael, MN (US); Mordechay Bleiwies, Kiryat Haim (IL); Mark Timothy Johnson, Mounds View, MN (US)

(73) Assignee: Galil Medical Inc., Arden Hills, MN (US)

( * ) Notice: Subject to any disclaimer, the term of this patent is extended or adjusted under 35 U.S.C. 154(b) by 581 days.

(21) Appl. No.: 14/627,568

(22) Filed: Feb. 20, 2015

(65) Prior Publication Data
US 2016/0242835 A1    Aug. 25, 2016

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/0262* (2013.01); *A61B 2018/0268* (2013.01); *A61B 2018/0281* (2013.01); *A61B 2018/0293* (2013.01)

(58) Field of Classification Search
CPC .......... A61B 18/02; A61B 2018/00041; A61B 2018/0262; A61B 2018/0268; A61B 2018/0281; A61B 2018/0293
See application file for complete search history.

(56) References Cited

U.S. PATENT DOCUMENTS

| | | | |
|---|---|---|---|
| 3,910,277 A | 10/1975 | Zimmer | |
| 4,444,156 A * | 4/1984 | Iwasaki | F24H 1/145 110/203 |
| 5,522,870 A * | 6/1996 | Ben-Zion | A61B 18/02 607/104 |
| 5,800,487 A | 9/1998 | Mikus et al. | |
| 5,800,488 A | 9/1998 | Crockett | |
| 5,916,212 A * | 6/1999 | Baust | A61B 18/02 606/22 |

(Continued)

FOREIGN PATENT DOCUMENTS

| | | |
|---|---|---|
| CA | 2261177 C | 5/2007 |
| EP | 925045 B1 | 4/2003 |

(Continued)

OTHER PUBLICATIONS

International Search Report and Written Opinion for International Application No. PCT/US2016/017828, dated May 31, 2016, 14 pages.

*Primary Examiner* — Jaymi E Della
(74) *Attorney, Agent, or Firm* — Fredrikson & Byron, P.A.

(57) ABSTRACT

A cryoneedle comprises an outer tube having a distal section with a generally central gas supply line placed within the outer tube. The gas supply line supplies a cryogas for forming an iceball on an outer surface of the outer tube over the distal section. The gas supply line terminates in an expansion chamber placed within the distal section. The cryoneedle comprises a heat exchange helix contacting the inner surface of the outer tube. The heat exchange helix has an increasing surface area per unit distance of the distal section such that the iceball has a generally symmetric shape.

31 Claims, 7 Drawing Sheets

(56) References Cited

U.S. PATENT DOCUMENTS

| | | | |
|---|---|---|---|
| 6,074,412 | A | 6/2000 | Mikus et al. |
| 6,270,476 | B1 | 8/2001 | Santoianni et al. |
| 6,505,629 | B1 | 1/2003 | Mikus et al. |
| 7,846,154 | B2 | 12/2010 | Bliweis et al. |
| 8,066,697 | B2 | 11/2011 | Zvuloni et al. |
| 2002/0111615 | A1* | 8/2002 | Cosman ............ A61B 18/1477 606/41 |
| 2003/0055416 | A1* | 3/2003 | Damasco ............ A61B 18/02 606/21 |
| 2005/0010200 | A1* | 1/2005 | Damasco ............ A61B 18/02 606/21 |
| 2007/0149959 | A1* | 6/2007 | DeLonzor ............ A61B 18/02 606/21 |
| 2009/0292280 | A1 | 11/2009 | Cytron et al. |
| 2010/0114275 | A1* | 5/2010 | Min ............ A61N 1/05 607/116 |
| 2010/0256620 | A1 | 10/2010 | Maytal |
| 2011/0022040 | A1* | 1/2011 | Geiselhart ............ A61B 18/02 606/23 |
| 2011/0264084 | A1* | 10/2011 | Reid ............ A61B 18/02 606/23 |
| 2012/0065630 | A1* | 3/2012 | Berzak ............ A61B 5/7232 606/21 |
| 2012/0289953 | A1* | 11/2012 | Berzak ............ A61B 18/02 606/23 |
| 2013/0204241 | A1* | 8/2013 | Baust ............ A61B 18/02 606/24 |
| 2014/0024909 | A1* | 1/2014 | Vij ............ A61B 5/055 600/373 |
| 2014/0135754 | A1 | 5/2014 | Berzak et al. |
| 2014/0194863 | A1 | 7/2014 | Berzak et al. |

FOREIGN PATENT DOCUMENTS

| | | |
|---|---|---|
| GB | 2336781 A | 11/1999 |
| WO | 2005000106 A2 | 1/2005 |
| WO | 2014144626 A2 | 9/2014 |

* cited by examiner

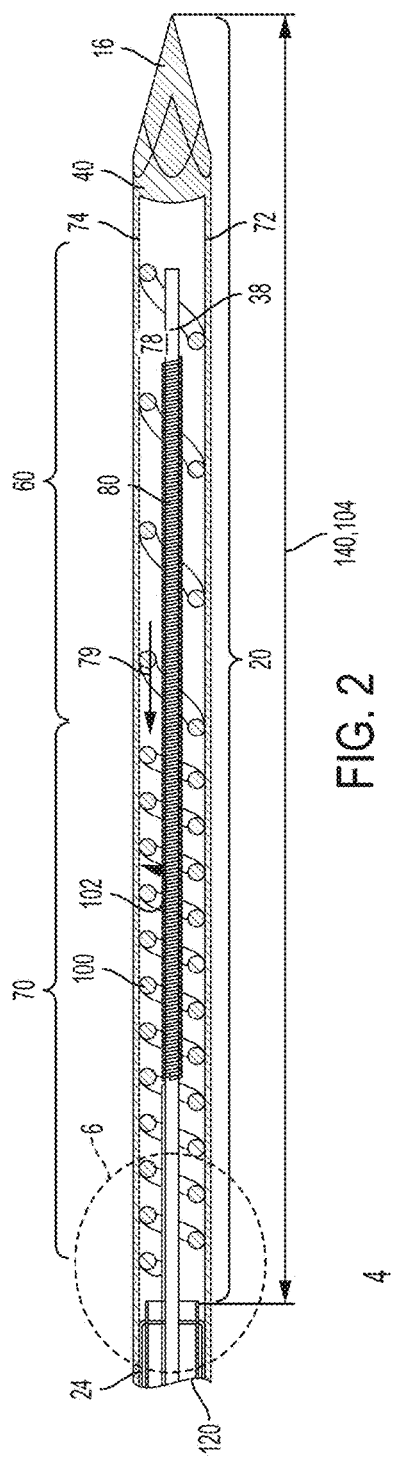

CRYONEEDLE

FIELD

This disclosure generally relates to a cryoneedle for forming iceballs having symmetric shapes.

BACKGROUND

Cryosurgical systems comprise one or more cryoneedle connected to one or more cryogas sources. Such systems are described in the commonly-assigned patent, U.S. Pat. No. 8,066,697 and in published application, U.S. Pub. No. 2010/0256620 A1, the disclosure of which is hereby incorporated by reference in its entirety. In such cryosurgical systems, a cryogas can be delivered from a cryogas source to one or more cryoneedles. The cryoneedle can be cooled or heated due to expansion of the cryogas, thereby freezing or thawing tissue in the vicinity of the cryoneedle.

SUMMARY

Certain embodiments include a cryoneedle comprising an outer tube having a distal section. The cryoneedle has a gas supply line positioned coaxially within the outer tube. The gas supply line can be configured to supply a cryogas for forming an ice ball on an outer surface of the outer tube over the distal section. The cryoneedle can have an expansion chamber placed within the distal section such that the central gas supply line terminates in the expansion chamber. The cryoneedle can have a heat exchange helix contacting the inner surface of the outer tube. The cryoneedle can have a return gas flow lumen defined annularly between the heat exchange helix and the central gas supply line adapted to carry cryogas from the expansion chamber toward the proximal section. The heat exchange helix can provide generally uniform cooling in the distal section such that the iceball is generally symmetric in shape.

In certain embodiments the heat exchange helix has an increasing surface area per unit distance of the distal section such that the iceball has a generally symmetric shape. In some cases, the return gas lumen provides a helical return path for the cryogas from the expansion chamber toward the proximal section.

Certain embodiments include a method of forming symmetric iceballs during cryosurgery. The method can comprise providing a cryosurgery system comprising a cryoneedle such as those described herein. The method involves supplying a cryogas through the gas supply line, expanding the cryogas at the expansion chamber, providing a helical return path for cryogas in the distal section, wherein the cryogas flows in the return gas flow lumen in a direction from the expansion chamber toward a proximal section, and forming an iceball on an outer surface of the outer tube over the distal section such that the iceball has a generally symmetric shape.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

FIG. 2 is an enlarged cross-sectional front view of portion 3 of the cryoneedle shown in FIG. 1A taken along the plane 2-2;

FIG. 3 is an enlarged perspective view of portion 3 of the cryoneedle shown in FIG. 1A with the outer tube removed from the view to illustrate internal components housed therein;

FIG. 7A is a front view of a cryoneedle according to certain embodiments illustrated with an ellipsoidal iceball formed at its distal tip; and FIG. 7B is a front view of a cryoneedle according to certain embodiments illustrated with a spherical iceball formed at its distal tip.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Cryosurgical systems can be used for cryoablating target tissues (e.g., a tumor). Typically, such systems include one or more cryoneedles, one or more cryogas sources and a controller. The cryogas sources can supply gases such as argon, nitrogen, air, krypton, CO2, CF4, xenon, and various other gases. The cryosurgical system can also include a controller having one or more sensors, flow meters, timers, analog/digital converters, wired or wireless communication modules, etc. Additionally, the controller can also regulate the flow rate, temperature and pressure of cryogas supplied to the cryoneedle.

During cryosurgery, for instance, a surgeon may deploy one or more cryoneedles such as those illustrated in FIG. 1 to cryoablate a target area of a patient anatomy by placing the cryoneedle 10 at or near the target area of the patient anatomy. In one example, cryoneedle 10 utilizes the Joule-Thomson effect to produce cooling or heating. In such cases, a cryogas expands in the cryoneedle 10 from a higher pressure to a lower pressure. Expansion of the cryogas results in temperatures at or below those necessary for cryoablating a tissue in the vicinity of the tip of the cryoneedle 10. Heat transfer between the expanded cryogas and the outer walls of the cryoneedle 10 can be used to form an iceball, and consequently cryoablate the tissue.

Figure 1A:
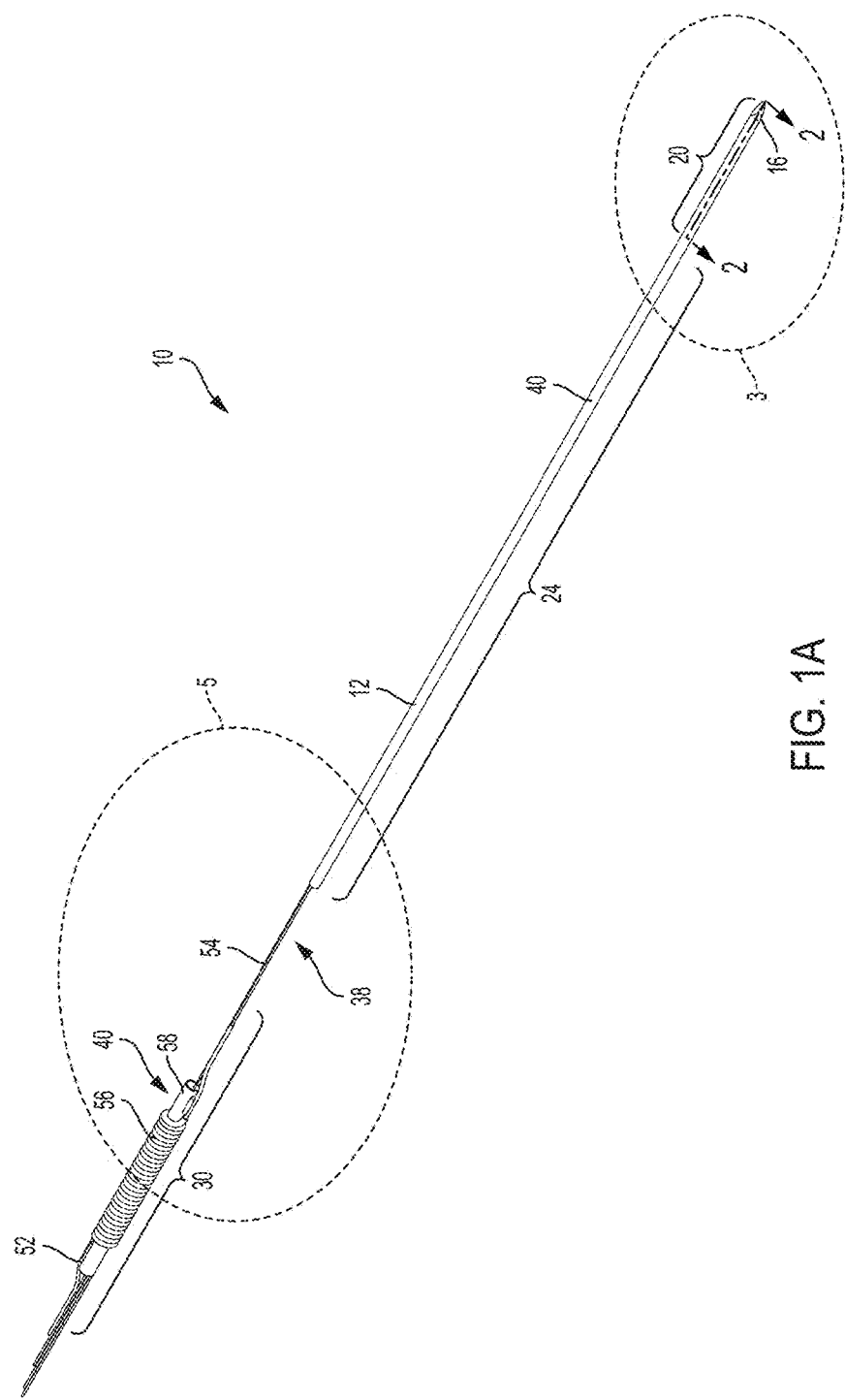
FIG. 1A is a perspective view of a cryoneedle according to an embodiment.
Figure 1B:
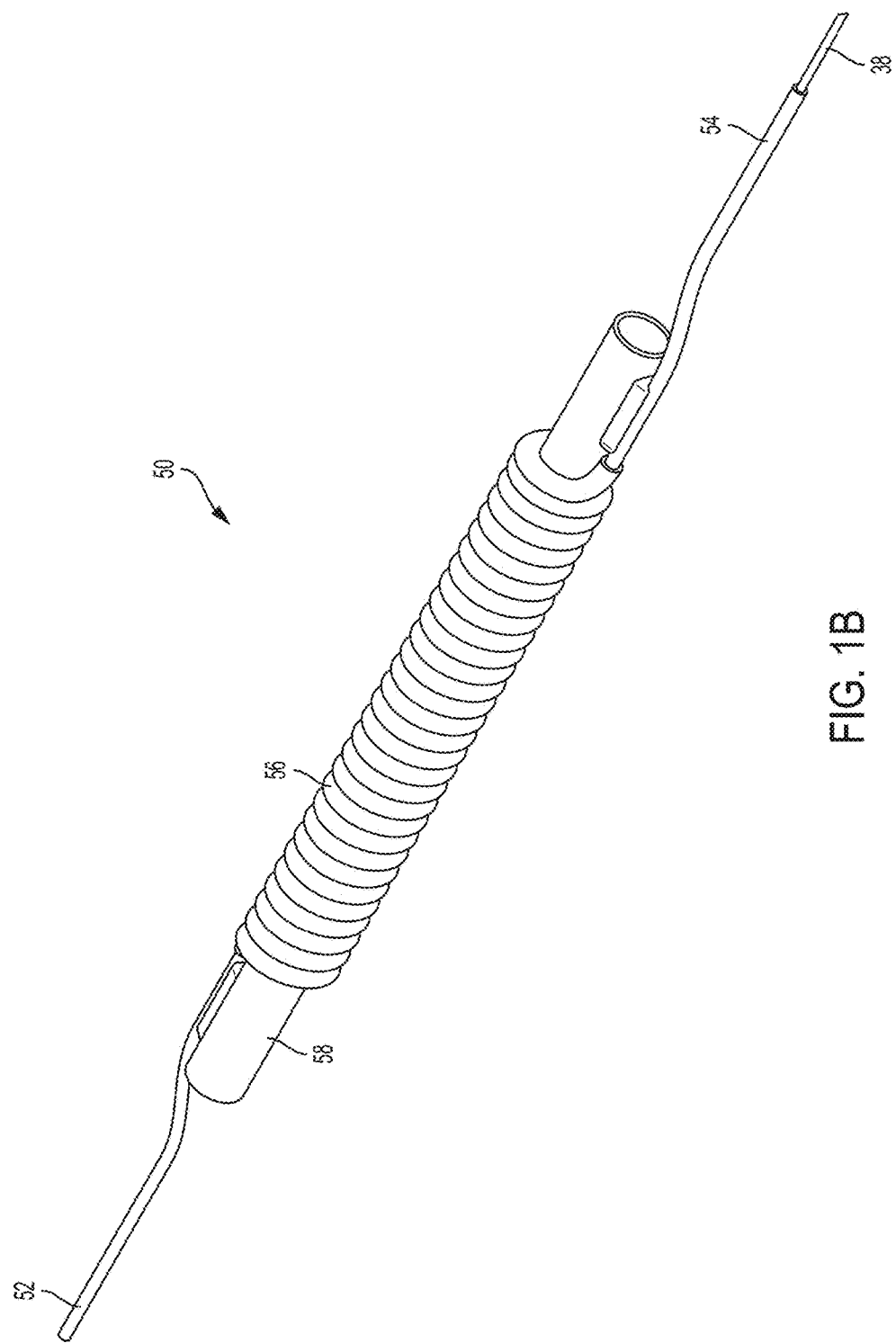
FIG. 1B is an enlarged perspective view of portion 1B of the cryoneedle shown in FIG. 1A.

As shown in FIGS. 1A-1B and 2, components of the cryoneedle 10 are located within an outer tube 12 (e.g., a trocar). The outer tube 12 can have a distal operating head 16 disposed at a distal section 20 of the cryoneedle 10 for penetrating through tissues of a patient during deployment. The outer tube 12 can be of substantially thin cross section for allowing deployment in tissues of a patient. In one example, the outer tube 12 has an outer diameter of about 2.1 millimeters. Other dimensions of the outer tube 12 are also contemplated. For example, the outer tube 12 can have an outer diameter of between about 1.5 millimeters and about 2.4 millimeters. As mentioned above, the outer tube 12 can have a distal section 20 placed at or near a target area of a patient's anatomy. The outer tube 12 can also have a middle section 24 positioned between the distal section 20, and a proximal section 30 of the cryoneedle 10. Additionally, the outer tube 12 has a longitudinal axis 34.

As seen in FIG. 2, the cryoneedle 10 includes a gas supply line 38 extending substantially along its length for providing a high-pressure gas to the distal operating head 16. The gas supply line 38 can be positioned coaxially/concentrically within the outer tube 12. The gas supply line 38 can be configured to supply a cryogas for forming iceballs on an outer surface 40 of the outer tube 12 over the distal section 20. In some cases, the gas supply line 38 can be a capillary tube. Referring to FIG. 1B, the gas supply line 38 comprises a proximal heat exchanger 50 positioned in the proximal section 30 of the cryoneedle 10 and operably connected to a cryogas source (not shown) at a first end 52 and the capillary tube at a second end 54. The proximal heat exchanger 50 can precool the cryogas from the cryogas source prior to being delivered to the middle and/or distal sections.

With continued reference to FIG. 1B, the proximal heat exchanger 50 can be a hollow helical tube 56 wound around a central core 58. The helical tube 56 of the proximal heat exchanger 50 provides increased heat exchange surface area per unit length of the helical tube 56 in comparison to heat exchangers that are not coiled. The helical tube 56 can be made of brass. Other metals such as stainless steel are also contemplated. In the illustrated embodiment shown in FIG. 1A, the proximal heat exchanger 50 is positioned far from the distal operating head 16. For instance, the proximal heat exchanger 50 can be positioned at a handle (not shown). In such cases, an insulating outer cover (not shown) can be positioned over the proximal heat exchanger 50 so as to facilitate manual deployment (e.g., by grasping the handle) by an operator (e.g., a surgeon). The insulating outer cover can be made of heat shrink plastic film. In some cases, the central core 58 can be substantially rigid in comparison to the distal operating head 16. Such embodiments can be beneficial in providing a cryoneedle 10 with a substantially flexible distal operating head 16 for penetrating soft tissue and a substantially rigid handle having a proximal heat exchanger 50 to precool the cryogas.

Referring to FIG. 2, the distal section 20 can have a first portion 60 and a second portion 70. The cryoneedle 10 can include an expansion chamber 72 within the first portion 60 of the distal section 20 such that the gas supply line 38 terminates in the expansion chamber 72. In some cases, the gas supply line 38 (e.g., capillary tube) can terminate in a joule-thomson orifice 74. The joule-thomson orifice 74 can be positioned near the expansion chamber 72. A high-pressure cryogas supplied via the gas supply line 38 exits gas supply line 38 via the joule-thomson orifice 74 and expands in the expansion chamber 72. As the cryogas expands in the expansion chamber 72, it cools rapidly and forms iceballs of different shapes and/or sizes over the outer surface 40 of the outer tube 12. The expansion of the cryogas can be such that when expanded, the cryogas is colder than the incoming cryogas.

Figure 4:
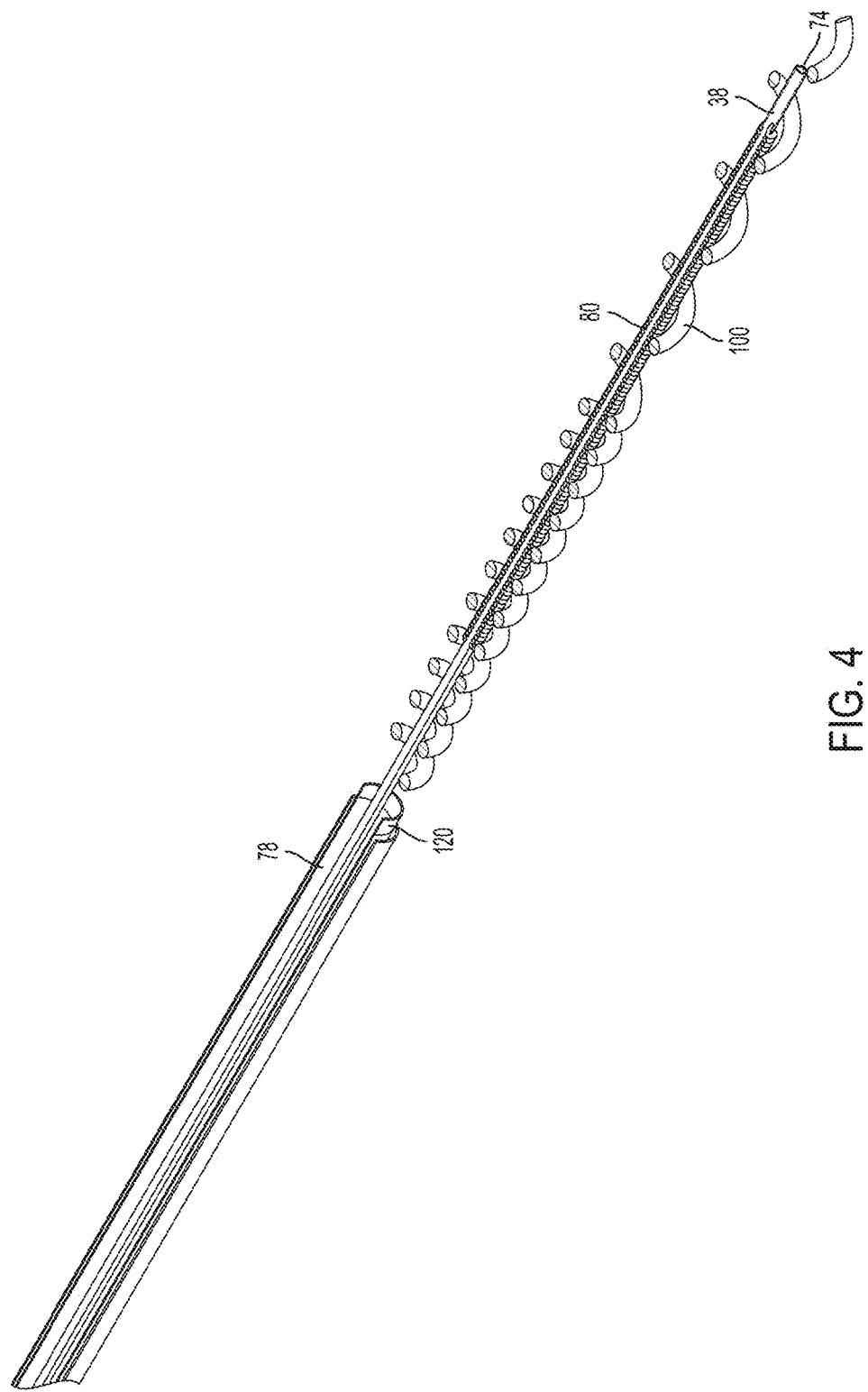
FIG. 4 is a cross-sectional view of the cryoneedle shown in FIG. 3 taken along the plane 4-4.
Figure 5:
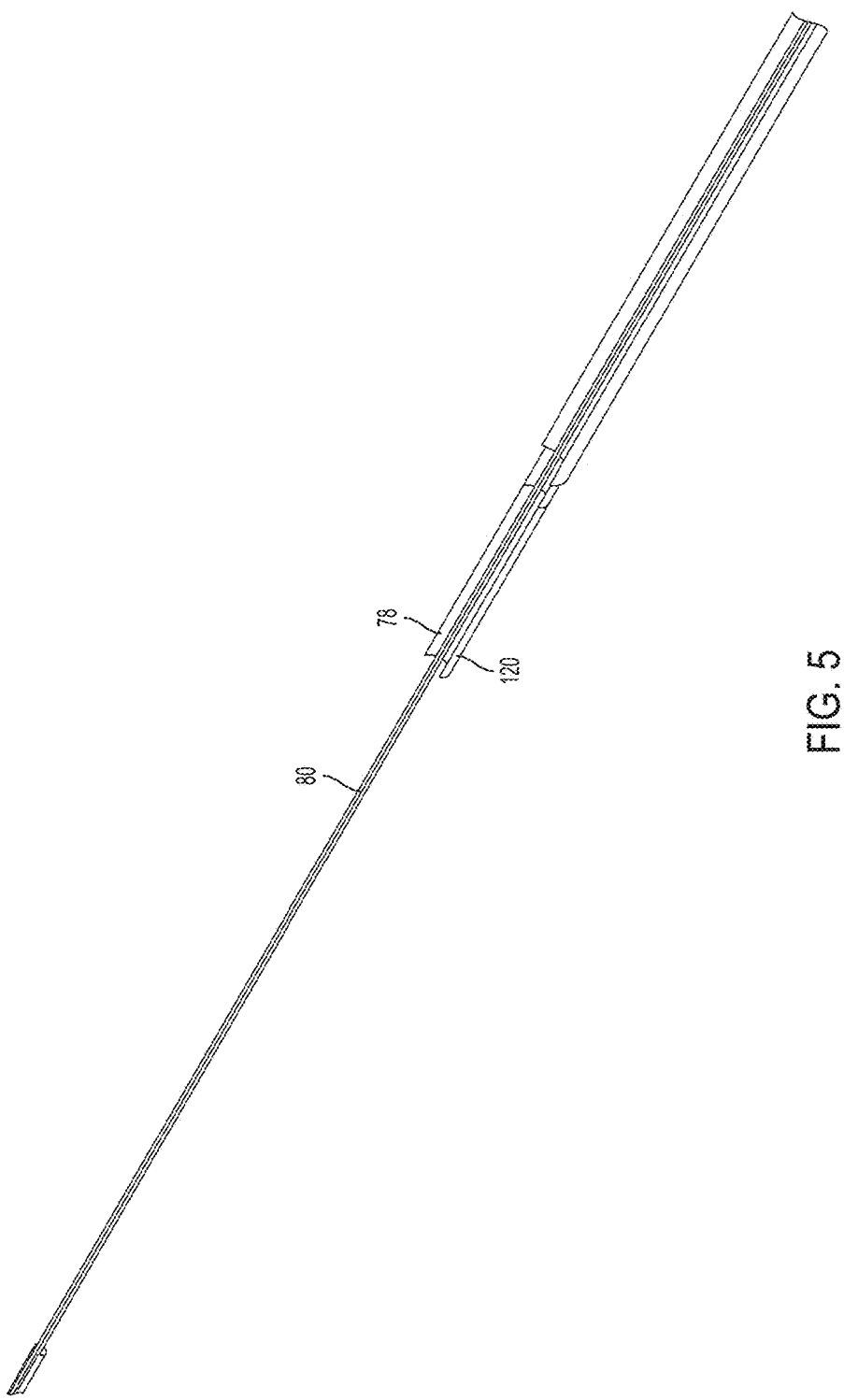
FIG. 5 is an enlarged perspective view of portion 5 of the cryoneedle shown in FIG. 1A with the outer tube removed from the view to illustrate internal components housed therein.

With continued reference to FIG. 2, the cryoneedle 10 comprises a return gas flow lumen 78 defined annularly between the heat exchange helix 100 and the central gas supply line 38. The return gas flow lumen 78 can carry cryogas from the expansion chamber 72 toward the proximal section 30 of the cryoneedle 10 along a return flow path 79 shown in FIG. 2. The return gas flow lumen 78 is defined along a return path of the cryogas between the gas supply line 38 and the inner wall 102 of the outer tube 12 of the cryoneedle 10. In certain embodiments as will be described below, the return gas flow lumen 78 is helical in shape. Referring now to FIGS. 4 and 5, and in operation, the cryogas expands in the expansion chamber 72, and the expanded cryogas flows in the return flow lumen, thereby cooling incoming cryogas flowing through the gas supply line 38. The expanded gas can subsequently be exhausted to the atmosphere near an end of the outer tube 12.

Referring back to FIG. 2, in some cases, a heater 80 can optionally be provided within the outer tube 12 near the distal section 20 to facilitate disengagement of cryoneedle 10 after cryoablating a tissue, for thawing a tissue at or near the distal section 20 of the cryoneedle 10, for cauterizing tissues, or for other purposes. As illustrated in this exemplary embodiment, an electrical heater 80 is provided coaxially with the gas supply line 38 and the outer tube 12 to facilitate heating the distal section 20 of the cryoneedle 10. Alternatively, the electrical heater 80 can be positioned elsewhere in cryoneedle 10 to heat the distal section 20 of the cryoneedle 10. The electrical heater 80 can be a resistive heater, wherein the electrical heater 80 generates heat proportional to the current flow therethrough and the electrical resistance of electrical heater 80. In such cases, as alluded to previously, the controller (not shown) can supply and/or regulate (e.g., with a Wheatstone bridge, ampere meter or voltmeter) electrical current flow to the electrical heater 80 within the cryoneedle 10. In the embodiment illustrated in FIG. 2, the electrical heater 80 comprises metal wires (e.g., copper) wound in helical coils (e.g., between about 50 coils and about 200 coils) around the gas supply tube. For instance, the wires are wound with a negligible pitch between adjacent coils of the wire. Additionally, the wires can substantially contact an outer surface 40 of the gas supply tube. While an electrical heater 80 is illustrated herein, alternative methods of heating the distal section 20 of the cryoneedle 10 are contemplated. For instance, the distal section 20 can instead be heated using a heating gas (e.g., a cryogas having an inversion temperature lower than temperature obtained by liquefaction of cooling gas) such as high-pressure helium supplied by a cryogas source. Alternatively, the distal section 20 of the cryoneedle 10 may not be heated and/or surrounding may not be tissue thawed.

As mentioned previously, the temperature of the cryogas can be colder in the first portion 60 of the distal section 20 (due to Joule-Thomson effect), than in the second portion 70, and heat transfer between the cryogas and the outer tube 12 can be higher over the first portion 60 than in the second portion 70. This can result in an iceball having an asymmetric shape (e.g., pear-shaped with the iceball generally tapering toward the second portion 70). To prevent asymmetric iceball formation, as seen in FIGS. 2 and 3, in one example, the cryoneedle 10 includes a heat exchange helix 100, comprising coils configured for enhancing heat exchange between the cryogas and the outer tube 12. The heat exchange helix 100 contacts the inner wall 102 of the outer tube 12 and is positioned coaxially with the outer tube 12. As perhaps best seen in FIG. 2, the coils of the heat exchange helix 100 are in contact with the inner wall 102 of the outer tube 12 and do not contact the heater 80 or the gas supply line 38 (e.g., capillary tube). These coils effectively act as fins on the inner wall 102 of the outer tube 12 and improve heat transfer to the outer tube 12 to form iceballs having symmetric shapes wherein the symmetry is about the longitudinal axis 34 of the outer tube 12.

With continued reference to FIGS. 2 and 3, the presence of heat exchange helix 100 on the inner wall 102 of the outer tube 12 increases the surface area over which return gas flows over from the expansion chamber 72 and toward the proximal section 30 of the cryoneedle 10. Moreover, the cryogas flows along a helical path from the expansion chamber 72 toward the proximal section 30 of the cryoneedle 10 resulting in enhanced heat exchange. Such embodiments result in higher heat transfer between the expanded cryogas and the outer tube 12, consequently providing a desired iceball shape and size (e.g., a symmetric shape such as sphere or ellipsoid) as will be described below. The heat exchange helix 100 enhances heat transfer over the distal section 20 by increasing surface area over which heat transfer occurs from the cryogas to the outer tube 12 of the cryoneedle 10. For example, the heat exchange helix 100 can provide a heat exchange surface area at the distal section 20 and permits heat transfer between the cryogas and the outer tube 12 such that the outer tube 12 is evenly cooled to a temperature of about −150 degree Celsius when the cryogas temperature is about −155 degree Celsius. Other temperatures are also contemplated. For instance, the outer tube 12 can be cooled to any temperature in the range of between about −145 degree Celsius and about −150 degree Celsius, when the cryogas temperature is between about −155 degree Celsius and about −150 degree Celsius.

The heat exchange helix 100 can provide generally uniform cooling over the entire length 104 of the distal section 20 such that the iceball (best illustrated in FIGS. 7A and 7B) is generally symmetric in shape. For instance, the heat exchange helix 100 can facilitate cooling the outer tube 12 evenly over the entire length 104 of the distal section 20 such that the heat transfer rate between the cryogas and the outer tube 12 is approximately constant over the entire length 104 of the distal section 20. As mentioned previously, the cryogas flowing in the return flow lumen over the first portion 60 can be at a lower temperature than the cryogas flowing in the return flow lumen over the second portion 70 because of rapid expansion of the cryogas near the Joule Thomson orifice and associate rapid cooling that occurs at the first portion 60. In such cases, the heat exchange helix 100 can increase heat transfer between cryogas and the outer tube 12 over the second portion 70 such that the heat transfer rate between the cryogas and the outer tube 12 over the first portion 60 roughly equals the heat transfer rate between the cryogas and the outer tube 12 over the second portion 70. Such embodiments can facilitate in generating iceballs having symmetric shape, and prevent formation of iceballs having asymmetric shapes (e.g., pear-shaped).

As seen in FIG. 3, the heat exchange helix 100 has a helix pitch. The helix pitch can be configured to generate an iceball 150 having a symmetrical shape (e.g., ellipsoidal or spherical). For example, as illustrated, the coils can have variable helix pitch. In FIG. 3, two helix pitches are shown: a first pitch 108 over the first portion 60 of the distal section 20 and a second pitch 110 over the second portion 70 of the distal section 20. The first pitch 108 can be greater than the second pitch 110 such that adjacent coils of the heat exchange helix 100 are spaced further apart in the first portion 60 than in the second portion 70. For instance, the heat exchange helix 100 can have fewer coils per unit length in the first portion 60 than in the second portion 70. In the illustrated embodiment, the heat exchange helix 100 has a higher surface area per unit length in the second portion 70 of the distal section 20 in comparison to the surface area per unit length in the first portion 60 of the distal section 20. As the cryogas has a higher temperature in the second portion 70 than in the first portion 60, the increased surface area in the second portion 70 facilitates heat transfer rates between the cryogas and the outer tube 12 that is roughly equal so that the iceball 150 (best illustrated in FIGS. 7A and 7B) has a generally symmetric shape. Alternatively, the helix pitch can be constant over the entire length 104 of the distal section 20.

In the embodiments illustrated herein, the heat exchange helix 100 is a coiled spring. The heat exchange helix 100 can be made of tin coated copper. Other metals and alloys (e.g., stainless steel) having sufficient resiliency and/or malleability so as to be formed into a helical shape of desired helix pitch are also contemplated.

Referring back to FIG. 2 and referring now to FIG. 4, the cryoneedle 10 comprises an insulating sheath 120 positionable at locations other than the distal section 20. The insulating sheath 120 abuts against the outer tube 12 to prevent the expanded cryogas returning from the expansion chamber 72 from coming into contact with the outer tube 12. For example, the cold return gas avoids contact with areas of the patient's body other than intended the target area such that an iceball 150 is therefore formed in the exposed region of the outer tube 12 (e.g., regions of the outer tube 12 not having the insulating sheath 120 positioned between the outer tube 12 and the return gas flow lumen 78). In the illustrated embodiment shown in FIG. 2, the entire length 104 of the distal section 20 is exposed. Over this exposed region length 140, the expanded cryogas contacts the outer tube 12 of the cryoneedle 10 and forms an iceball 150. The insulated sheath is positioned over the entire length of the middle section 24 of the cryoneedle 10 in this embodiment. Over the entire length of the middle section 24, the cryogas is prevented from contacting the outer tube 12, thereby preventing cooling of tissue surrounding the middle section 24 and/or iceball formation thereon.

In some cases, the exposed region length 140 (best seen in FIG. 2) of the outer tube 12 can determine the shape of the iceball. FIGS. 7A and 7B for instance illustrate an ellipsoidal and a spherical iceball 150 formed over the distal section 20 of the cryoneedle 10, respectively. In one example, when the exposed region length 140 of the outer tube 12 is about 34 millimeters, the iceball 150 can have a substantially ellipsoidal shape such as that illustrated in FIG. 7A. In another example, when the exposed region length 140 of the outer tube 12 is about 18 millimeters, the iceball 150 can have a substantially spherical shape such as that illustrated in FIG. 7B. While in both FIGS. 7A and 7B, the iceball 150 formed is of a symmetric shape, the exposed region length 140 of the outer tube 12 (e.g., not covered by the insulating sheath 120) influences the aspect ratio 160 of the iceball 150 shape. For example, a shorter exposed region length produces a spherical iceball 150 and a longer exposed region length produces an ellipsoidal iceball. By shortening or extending the length of the insulating sheath 120, various symmetric shapes can be obtained. The exposed region length 140 can thus be varied to change an aspect ratio 160 of the iceball 150. As illustrated in FIGS. 7A and 7B, aspect ratio 160 of the iceball 150 can be defined as the ratio of length 162 of the iceball 150 measured along the lengthwise direction of the cryoneedle 10 and the width 164 of the iceball 150 measured in a direction perpendicular to the lengthwise direction of the cryoneedle 10. As illustrated, an aspect ratio 160 of about one implies a spherical iceball 150.

Figure 6:
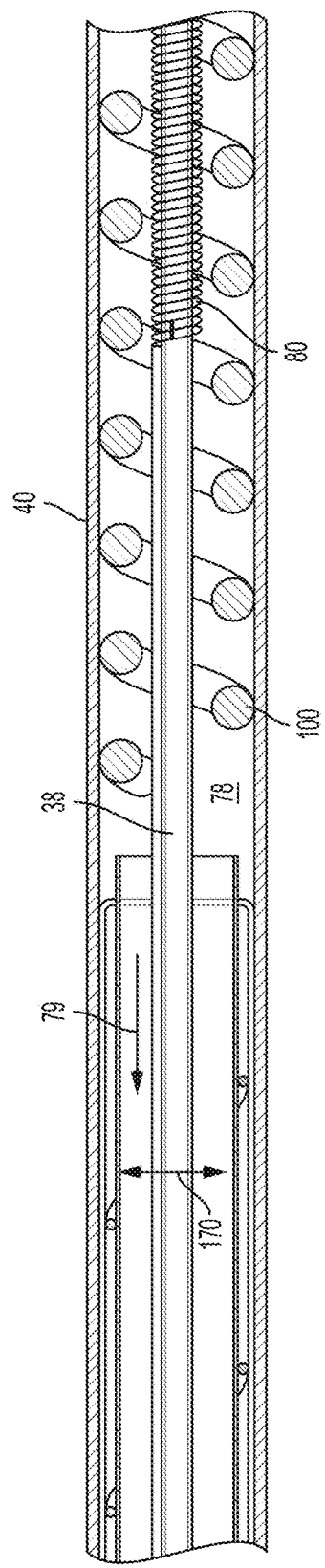
FIG. 6 is an enlarged perspective view of portion 6 of the cryoneedle shown in FIG. 2.

In some exemplary cases, the heat exchange helix 100 disclosed herein can create additional resistance to flow of expanded cryogas in the return gas flow lumen 78. In such cases, the dimensions of the cryoneedle 10 can be configured to prevent excessive flow resistance and/or back pressure being generated in the cryoneedle 10. Referring now to FIGS. 5 and 6, the insulating sheath 120 can have dimensions suitable to permit the return flow of expanded cryogas from the distal section 20 toward the proximal section 30. For instance, the insulating sheath 120 can have an inner diameter 170 sufficient to create an annular gap between the gas supply line 38 and an outer wall of the insulating sheath 120 as best seen in FIGS. 5 and 6. The annular gap being in fluid communication with the return gas flow lumen 78 to receive cryogas flowing therethrough. In one example, the inner diameter 170 of the insulating sheath 120 is about 1.32 mm. In other examples, the insulating sheath 120 can have an inner diameter 170 between about 0.5 millimeters and about 2 millimeters. In one example, when the outer diameter of the outer tube 12 is about 2.1 millimeters, the insulating sheath 120 can have an inner diameter 170 of between about 1.0 millimeter and about 1.4 millimeters. In another example, when the outer diameter of the outer tube 12 is about 1.5 millimeters, the insulating sheath 120 can have an inner diameter 170 of about 0.72 millimeters. In another example, when the outer diameter of the outer tube 12 is about 2.4 millimeters, the insulating sheath 120 can have an inner diameter 170 of between about 1.25 millimeters and about 1.7 millimeters. The inner diameter 170 of the insulating sheath 120 can therefore be sufficiently large to minimize back pressure acting on the expanded cryogas flowing through the annular gap from the return gas flow lumen 78. In such cases, backpressure is minimized to allow the pressure of the expanding cryogas to fall as low as possible (e.g., zero gauge), which results in a lower gas temperature and bigger iceball. Maximizing the inner diameter 170 of the insulating sheath 120 helps to minimize the overall backpressure of the cryoneedle 10.

Certain embodiments include a method of forming ice balls having a symmetric shape during cryosurgery. The method can comprise the step of providing a cryosurgery system such as those disclosed herein, supplying a cryogas through the gas supply line 38, expanding the cryogas in the expansion chamber 72, providing a helical return path for cryogas in the distal section 20, the cryogas flowing in the return gas flow lumen 78 in a direction from the expansion chamber 72 toward a proximal section 30, and forming an iceball 150 on an outer surface 40 of the outer tube 12 over the distal section 20 such that the iceball 150 has a generally symmetric shape.

Embodiments of the cryoneedle 10 disclosed herein can provide several advantages. The cryoneedle 10 can be configured such that substantially symmetric iceballs having desirable shapes. The cryoneedle 10 can enhance heat transfer over portions of its distal section 20 such that desirable iceball characteristics (e.g., symmetry, size and shape) can be obtained with a smaller needle outer tube 12 diameter. Moreover, because of the smaller needle outer tube 12 diameter, the weight and torque on the needle handle are also minimized making the cryoneedle 10 easily deployable during cryosurgery.

Thus, embodiments of cryoneedle 10 with evenly distributed cooling are disclosed. Although the present embodiments have been described in considerable detail with reference to certain disclosed embodiments, the disclosed embodiments are presented for purposes of illustration and not limitation. One skilled in the art will appreciate that various changes, adaptations, and modifications may be made without departing from the spirit of the invention.

What is claimed is:

1. A cryoneedle comprising:
    an outer tube having a distal section and a longitudinal axis;
    a gas supply line positioned within the outer tube, the gas supply line configured to supply a cryogas for forming an ice ball on an outer surface of the outer tube over the distal section, the gas supply line having a cryogas outlet;
    an expansion chamber located within the distal section such that the gas supply line terminates in the expansion chamber, the cryogas outlet being positioned in the expansion chamber;
    an electrical resistance heater configured to heat tissue, when current is supplied thereto, the electrical resistance heater comprising a wire wound around the gas supply line into helical coils, the electrical resistance heater being located within the distal section of the outer tube;
    a heat exchange helix contacting an inner surface of the outer tube, the heat exchange helix extending longitudinally in a distal direction past the cryogas outlet in the distal section; and
    a return gas flow lumen defined annularly between the heat exchange helix and the gas supply line adapted to carry the cryogas from the expansion chamber along a return flow path,
    the heat exchange helix adapted to provide generally uniform rate of heat transfer in the distal section such that the ice ball formed on the outer surface of the outer tube is generally symmetric in shape along the longitudinal axis of the outer tube.

2. The cryoneedle of claim 1, wherein the electrical resistance heater is positioned coaxially and in contact with the gas supply line.

3. The cryoneedle of claim 2, wherein the heat exchange helix is positioned coaxially with an axis of the outer tube.

4. The cryoneedle of claim 1, wherein the return gas flow lumen is helical in shape.

5. The cryoneedle of claim 1, wherein the outer tube has an outer diameter of about 2.1 millimeters.

6. The cryoneedle of claim 1, wherein the expansion chamber is adapted to expand the cryogas, and the expanded cryogas flowing in the return gas flow lumen is adapted to cool the cryogas flowing through the gas supply line.

7. The cryoneedle of claim 1, wherein the heat exchange helix has a helix pitch defined axially between adjacent turns of the heat exchange helix, the helix pitch being configurable along the heat exchange helix to generate an iceball having an ellipsoidal or a spherical shape.

8. The cryoneedle of claim 7, wherein the helix pitch along the heat exchange helix is constant substantially over the distal section.

9. The cryoneedle of claim 7, wherein the helix pitch has a first pitch over a first portion of the distal section and a second pitch over a second portion of the distal section.

10. The cryoneedle of claim 9, wherein the first pitch is greater than the second pitch, such that the cryogas enhances heat transfer over the second portion of the distal section such that the iceball has a symmetric shape.

11. The cryoneedle of claim 1, wherein the heat exchange helix is a helical spring.

12. The cryoneedle of claim 11, wherein the heat exchange helix is made of a metal alloy comprising copper and tin.

13. The cryoneedle of claim 1, wherein the heat exchange helix has a heat exchange surface area at the distal section, the heat exchange surface area providing sufficient heat transfer between the cryogas and the outer tube such that the outer tube is cooled to a temperature of between about −150 degree Celsius and about −145 degree Celsius when the cryogas temperature is about −155 degree Celsius and about −150 degree Celsius respectively.

14. The cryoneedle of claim 1, further comprising an insulating sheath substantially surrounding the gas supply line and thereby forming a barrier between the return gas flow lumen and the outer tube over a portion of a length of the outer tube, the insulating sheath having an inner diameter sufficient to create an annular gap between the gas supply line and an inner wall of the insulating sheath, the annular gap being in fluid communication with the return gas flow lumen to receive the cryogas flowing therethrough.

15. The cryoneedle of claim 14, wherein the inner diameter of the insulating sheath is about 1.32 mm.

16. The cryoneedle of claim 14, wherein the insulating sheath surrounds the gas supply line over the portion of the length of the outer tube such that the expanded cryogas is configured to directly contact the outer tube over an exposed region, the exposed region having an exposed region length, the exposed region length adapted to generate an iceball having a predetermined aspect ratio.

17. The cryoneedle of claim 14, wherein the annular gap defined between the insulating sheath and the gas supply line has a diameter sufficient to minimize back pressure acting on the expanded cryogas flowing through the annular gap from the return gas flow lumen.

18. The cryoneedle of claim 1, wherein the gas supply line is coaxial with the longitudinal axis of the outer tube.

19. The cryoneedle of claim 1, wherein the heat exchange helix contacts the inner surface of the outer tube at the distal section.

20. The cryoneedle of claim 1, wherein a distal end of the heat exchange helix terminates between the cryogas outlet and a distal operating tip of the distal section of the cryoneedle.

21. The cryoneedle of claim 1, wherein an inner diameter of the heat exchange helix is greater than an outer diameter of the electrical resistance heater such that the return gas flow lumen is defined annularly between the heat exchange helix and the electrical resistance heater.

22. The cryoneedle of claim 1, wherein the heat exchange helix extends past the electrical resistance heater in the distal section and/or in a proximal section opposite to the distal section.

23. A cryoneedle, comprising:
a needle shaft having a proximal section and a distal section opposite to the proximal section, the distal section being insertable into a patient;
a cryofluid supply tube located within the needle shaft, the cryofluid supply tube being configured to receive a cryofluid from a cryofluid source, the cryofluid supply tube being configured to supply the cryofluid toward the distal section for cooling and/or freezing patient tissue;
an electrical resistance heater configured to heat the patient tissue, when current is supplied thereto, the electrical resistance heater comprising a wire wound in helical coils within the distal section of the needle shaft, the helical coils including a first helical coil and a second helical coil, the first helical coil and the second helical coil being coaxial, the wire extending from an end of the first helical coil and looping back to an end of the second helical coil to connect the first helical coil to the second helical coil by a looped section, the looped section being positioned in the distal section of the needle shaft, whereby, when current is supplied to the electrical resistance heater, current flows towards and loops back in the looped section,
the looped section being positioned distally to both the first helical coil and the second helical coil;
a heat exchange helix wrapping around the electrical resistance heater, the heat exchange helix being positioned between an inner surface of the needle shaft and the electrical resistance heater; and
a return gas flow lumen in contact with the heat exchange helix, to permit passage of the cryofluid from the distal section toward the proximal section.

24. The cryoneedle of claim 23, wherein a distal end of the first helical coil is connected to a distal end of the second helical coil to form the looped section.

25. The cryoneedle of claim 24, wherein the distal end of the first helical coil is positioned distally to the distal end of the second helical coil.

26. The cryoneedle of claim 23, wherein the ends of the first and second helical coils wrap helically in the same direction around the cryofluid supply tube.

27. A cryoneedle comprising:
an outer tube having a distal section and a longitudinal axis;
a gas supply line positioned within the outer tube, the gas supply line configured to supply a cryogas for forming an ice ball on an outer surface of the outer tube over the distal section, the gas supply line having a cryogas outlet;
an expansion chamber located within the distal section such that the gas supply line terminates in the expansion chamber, the cryogas outlet being positioned in the expansion chamber;
an electrical resistance heater configured to heat tissue, when current is supplied thereto, the electrical resistance heater comprising a wire wound around the gas supply line into helical coils, the electrical resistance heater being located within the distal section of the outer tube;
a heat exchange helix contacting an inner surface of the outer tube, the heat exchange helix extending longitudinally in a distal direction past the cryogas outlet in the distal section; and
a return gas flow lumen defined between the heat exchange helix and the gas supply line adapted to carry the cryogas from the expansion chamber along a return flow path,
the heat exchange helix having at least a first portion with a constant number of turns per unit distance such that the ice ball formed on the outer surface of the outer tube is generally symmetric in shape along the longitudinal axis of the outer tube.

28. The cryoneedle of claim 27, wherein the heat exchange helix comprises a second portion with another constant number of turns per unit distance.

29. The cryoneedle of claim 28, wherein the first portion of the heat exchange helix extends past the cryofluid supply tube.

30. The cryoneedle of claim 29, wherein the second portion of the heat exchange helix is proximal to the first portion of the heat exchange helix and/or the cryogas outlet.

31. A cryoneedle comprising:

an outer tube having a distal section placed at or near a target area of a patient's anatomy and a longitudinal axis;

a gas supply line positioned within the outer tube, the gas supply line configured to supply a cryogas for forming an ice ball on an outer surface of the outer tube over the distal section;

an expansion chamber located within the distal section such that the gas supply line terminates in the expansion chamber;

an electrical resistance heater provided coaxially with the gas supply line and the outer tube to facilitate heating of the distal section of the cryoneedle;

a heat exchange helix contacting the inner surface of the outer tube, the heat exchange helix not contacting either the electrical resistance heater or the gas supply line; and a return gas flow lumen defined annularly between the heat exchange helix and the gas supply line to carry the cryogas from the expansion chamber along a return flow path, the heat exchange helix providing a generally uniform rate of heat transfer in the distal section such that the iceball formed on the outer surface of the outer tube is generally symmetric in shape along the longitudinal axis of the outer tube.

* * * * *